(12) United States Patent
Kim et al.

(10) Patent No.: US 11,166,891 B2
(45) Date of Patent: Nov. 9, 2021

(54) BIS PHENYL HEXA TRIEN DERIVATIVES, PREPARATION METHOD THEREOF, AND COMPOSITION FOR SKIN WHITENING CONTAINING THE SAME AS AN ACTIVE INGREDIENT

(71) Applicant: Korea Research Institute of Chemical Technology, Daejeon (KR)

(72) Inventors: Woo-Keun Kim, Daejeon (KR); Sangwoo Lee, Daejeon (KR); Seokjoo Yoon, Daejeon (KR); Chul Min Park, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 16/562,298

(22) Filed: Sep. 5, 2019

(65) Prior Publication Data
US 2020/0078279 A1 Mar. 12, 2020

(30) Foreign Application Priority Data
Sep. 6, 2018 (KR) .................. 10-2018-0106614

(51) Int. Cl.
| | |
|---|---|
| *C07C 43/215* | (2006.01) |
| *A61K 8/33* | (2006.01) |
| *C07C 43/285* | (2006.01) |
| *C07C 41/30* | (2006.01) |
| *A23L 33/10* | (2016.01) |
| *A61Q 19/02* | (2006.01) |

(52) U.S. Cl.
CPC ............... *A61K 8/33* (2013.01); *A23L 33/10* (2016.08); *A61Q 19/02* (2013.01); *C07C 41/30* (2013.01); *C07C 43/285* (2013.01); *A23V 2002/00* (2013.01); *C07C 2601/16* (2017.05)

(58) Field of Classification Search
CPC ..... C07C 43/215; C07C 43/285; C07C 41/30; C07C 2601/16; A23L 33/10; A61Q 19/02
See application file for complete search history.

(56) References Cited

FOREIGN PATENT DOCUMENTS

KR 20130060496 6/2013

OTHER PUBLICATIONS

Ha et al, titel: Molecular Docking Studies of (1E,3E,5E)-1,6-Bis(substituted phenyl)-hexa-1,3,5-triene and 1,4-bis(substituted trans-styryl)benzene analogs as novel tyrosinase inhibitors, Biol. Pharm. Bull.; vol. 36; No. 1; pp. 55-65, published Jan. 2013. (Year: 2013).*
Loizzo et al, title: Natural and Synthetic Tyrosinase Inhibitors as Antibrowning Agents: An Update, Comprehensive Reviews in Food Science and Food Safety; vol. 11, 2012; pp. 378-389 (Year: 2012).*
Monteiro et al ; title: A Comparative Study of the Efficacy of 4% Hydroquinone vs 0.75% Kojic Acid Cream in the Treatment of Facial Melasma; Indian J Dermatol. Mar.-Apr. 2013; vol. 58, No. 2, 157. (Year: 2013).*
Oh, et al. "Novel (1E,3E,5E)-1,6-bis(Substituted phenyl)hexa-1,3,5-triene Analogs Inhibit Melanogenesis in B16F10 Cells and Zebrafish" International Journal of Molecular Sciences, 2018, 19, 1067, 12 pages.
Halaouli et al. "Fungal tyrosinases: new prospects in molecular characteristics, bioengineering and biotechnical applications" Journal of Applied Microbiology, 2006, pp. 219-232.
Cayce et al. "Hyperpigmentation: a review of common treatment options", Journal of Drugs in Dermatology, 2004, pp. 668-673.
Fenoll et al., The International Journal of Biochemistry & Cell Biology, vol. 36, Issue 2, Feb. 2004, pp. 235-246, Oct. 17, 2003, Jul. 22, 2003.

* cited by examiner

*Primary Examiner* — Yanzhi Zhang
(74) *Attorney, Agent, or Firm* — Workman Nydegger

(57) ABSTRACT

The present invention relates to a bis phenyl hexa triene derivative, a preparation method thereof and a composition for skin whitening comprising the same as an active ingredient. The said derivative inhibits the expression of tyrosinase, TRP 1 (tyrosinase-related protein 1), TRP 2 (tyrosinase-related protein 2) or MITF (microphthalmia-associated transcription factor) gene which produces a precursor necessary for the generation of melanin, suppresses the activity of tyrosinase, eventually inhibits the biosynthesis of melanin, is safe due to low cytotoxicity, and has less side effects and excellent antioxidative effect, so that it can be effectively used as a composition for skin whitening.

14 Claims, 9 Drawing Sheets

Specification includes a Sequence Listing.

BIS PHENYL HEXA TRIEN DERIVATIVES, PREPARATION METHOD THEREOF, AND COMPOSITION FOR SKIN WHITENING CONTAINING THE SAME AS AN ACTIVE INGREDIENT

CROSS-REFERENCE TO RELATED APPLICATIONS

This application claims priority to Korea Application No. 10-2018-0106614, filed Sep. 6, 2018, entitled "BIS PHENYL HEXA TRIEN DERIVATIVES, PREPARATION METHOD THEREOF, AND COMPOSITION FOR SKIN WHITENING CONTAINING THE SAME AS AN ACTIVE INGREDIENT", which application is incorporated by reference herein in its entirety.

REFERENCE TO A SEQUENCE LISTING SUBMITTED VIA EFS-WEB

The content of the ASCII text file of the sequence listing named "18931-16_2019-11-22_sequence-listing_ST25", which is 2.38 kb in size with a created date of Nov. 22, 2019, is electronically submitted herewith the application and is incorporated herein by reference in its entirety.

BACKGROUND OF THE INVENTION

Field of the Invention

The present invention relates to a bis phenyl hexa triene derivative, a preparation method thereof and a composition for skin whitening comprising the same as an active ingredient. Particularly, the composition for skin whitening includes a pharmaceutical composition for skin whitening, a cosmetic composition for skin whitening and a health functional food for skin whitening.

Description of the Related Art

Human skin color is determined largely by melanin, hemoglobin, carotene, etc., and melanin plays the most important role. Melanin is a black pigment found in animals, plants, and microorganisms. Melanin is not essential for growth or development of living things but it is a substance that enhances viability and competitiveness in environment. Melanin is a stable pigment among the pigments found in organisms and is not soluble in almost all solvents. It is known that the melanogenesis process occurs in melanosomes, the organelles of the specifically differentiated cells, melanocytes. That is, skin color is determined by the content and distribution of melanin, and related to the number and distribution of melanosomes released extracellularly after generated in melanocytes. Although melanin has a good function to protect the skin from ultraviolet light, it is known to be an important factor in inducing melanomas and hyperpigmentation such as melasma and freckles when it is overproduced (J. Drugs Dermatol., 2004, 3, 668-678).

The in vivo synthesis process of melanin is as follows. Melanin (Eumelanin or Pheomelanin) is generated as a copolymer by using tyrosine as a substrate by tyrosinase, TRP 1 (tyrosinase-related protein 1) and TRP 2 (tyrosinase-related protein 2) via auto-oxidation reaction in melanosomes of melanocytes, the cells synthesizing melanin (see FIG. 1). At this time, the expression of tyrosinase, TRP1 and TRF2 is accelerated by MITF (microphthalmia-associated transcription factor). The generated melanin is transferred to keratinocytes through melanosomes. After 28 days of keratinization in keratinocytes, melanin comes to the surface of the skin. However, in this process, when melanin is overproduced due to factors promoting melanin production, the cycle of keratinization is physiologically prolonged, and melanin is not removed from skin along with keratin, leading to pigmentation. So, to prevent this phenomenon of pigmentation, some processes in the process of melanin production need to be controlled.

Tyrosinase (EC 1.14.18.1) is the most important enzyme for melanin biosynthesis in plant, microorganism and mammalian cells, which converts tyrosine into DOPA Quinone, a key precursor of melanin biosynthesis. This enzyme has a monophenolase function to convert L-tyrosine into L-DOPA (3,4-dihydroxyphenylalanin) and a diphenolase function to convert L-DOPA into L-DOPA Quinone (J. Appl. Microbiol., 2006, 100, 219-232; Int. J. Biochem. Cell Biol., 2004, 36, 235-246). The produced DOPA Quinone is automatically converted into melanin without any aid of enzymatic action. Therefore, by inhibiting the activity of tyrosinase, melanin biosynthesis can be inhibited.

There are several mechanisms involved in inhibiting melanin synthesis. One of the most representative processes to inhibit melanin synthesis is to inhibit the activity of tyrosinase, the enzyme playing an important role in melanin synthesis. An example of the commercialized pigmentation inhibitor is a chelator such as kojic acid having copper ions as an active site which inhibits the activity of tyrosinase or a substance having a similar structure to tyrosine, a substrate of tyrosinase such as arbutin which inhibits melanin synthesis by competitively reacting to tyrosinase with tyrosine. However, most of the whitening materials have low stability so that the effect does not last long, suggesting that they are limited in application to the product.

SUMMARY OF THE INVENTION

It is an object of the present invention to provide a bis phenyl hexa triene derivative.

It is another object of the present invention to provide a preparation method of a bis phenyl hexa triene derivative.

It is also an object of the present invention to provide a pharmaceutical composition for skin whitening comprising a bis phenyl hexa triene derivative as an active ingredient.

It is further an object of the present invention to provide a cosmetic composition for skin whitening comprising a bis phenyl hexa triene derivative as an active ingredient.

It is also an object of the present invention to provide an antioxidative composition comprising a bis phenyl hexa triene derivative as an active ingredient.

It is also an object of the present invention to provide a health functional food for skin whitening comprising a bis phenyl hexa triene derivative as an active ingredient.

To achieve the above objects, in an aspect of the present invention, the present invention provides a compound represented by formula 1 below, an optical isomer thereof or a pharmaceutically acceptable salt thereof:

[Formula 1]

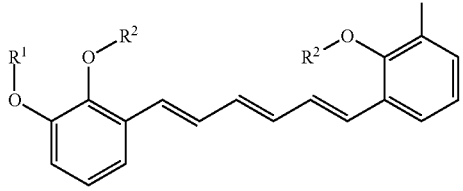

(In formula 1,

R[1] and R[2] are independently straight or branched $C_{1-6}$ alkyl).

In another aspect of the present invention, the present invention provides a preparation method of a compound represented by formula 1 comprising a step of preparing a compound represented by formula 1 by reacting a compound represented by formula 3 with a compound represented by formula 4 as shown in reaction formula 1 below:

[Reaction Formula 1]

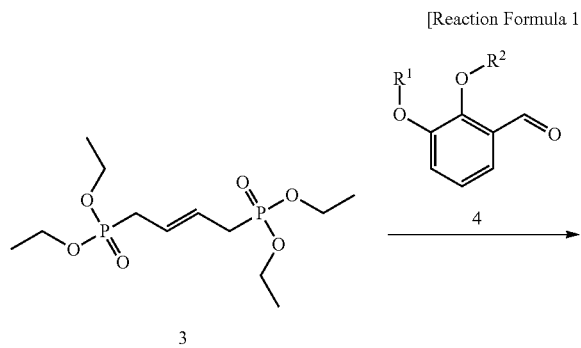

(In reaction formula 1,

R[1] and R[2] are as defined in formula 1 above).

In another aspect of the present invention, the present invention provides a cosmetic composition for skin whitening comprising a compound represented by formula 1 below or a pharmaceutically acceptable salt thereof as an active ingredient:

[Formula 1]

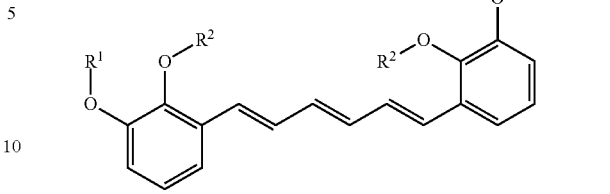

(In formula 1,

R[1] and R[2] are independently straight or branched $C_{1-6}$ alkyl).

In another aspect of the present invention, the present invention provides a cosmetic composition for skin whitening comprising a compound represented by formula 1 below, an optical isomer thereof or a pharmaceutically acceptable salt thereof as an active ingredient:

[Formula 1]

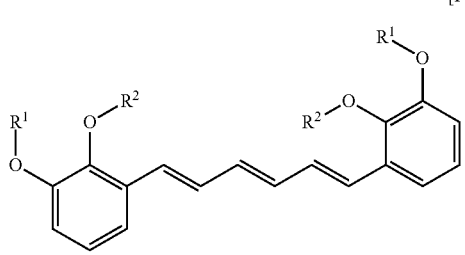

(In formula 1,

R[1] and R[2] are independently straight or branched $C_{1-6}$ alkyl).

In another aspect of the present invention, the present invention provides an antioxidative composition comprising a compound represented by formula 1 below, an optical isomer thereof or a pharmaceutically acceptable salt thereof as an active ingredient:

[Formula 1]

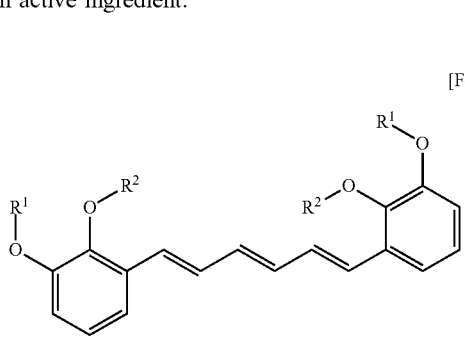

(In formula 1,

R[1] and R[2] are independently straight or branched $C_{1-6}$ alkyl).

In another aspect of the present invention, the present invention provides a health functional food for skin whitening comprising a compound represented by formula 1 below, an optical isomer thereof or a pharmaceutically acceptable salt thereof as an active ingredient:

[Formula 1]

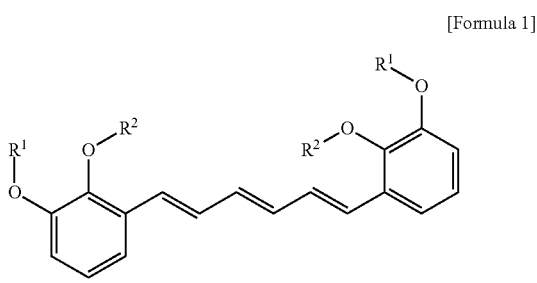

(In formula 1,
R¹ and R² are independently straight or branched $C_{1-6}$ alkyl).

Advantageous Effect

The compound represented by formula 1 of the present invention is excellent in inhibiting the expression of tyrosinase, TRP 1 (tyrosinase-related protein 1), TRP 2 (tyrosinase-related protein 2) or MITF (microphthalmia-associated transcription factor) gene which produces a precursor necessary for the generation of melanin even at a low concentration and is also excellent in suppressing the activity of tyrosinase, so that it eventually inhibits the production of melanin. In addition, the cell survival rate is maintained at about 80% even when the concentration of the compound according to the present invention is increased, that is, the compound has a significantly low cytotoxicity indicating that the compound is safe, and has low side effects and excellent antioxidative effects. Therefore, the compound of the present invention can be effectively used as a pharmaceutical composition for skin whitening, a cosmetic composition for skin whitening, a health functional food for skin whitening, and an antioxidative composition.

BRIEF DESCRIPTION OF THE DRAWINGS

FIG. 4 is a set of graphs illustrating the inhibitory effect of the compound of the present invention on TRP 1 and TRP 2 gene expression, evaluated in Experimental Example 3 (vertical axis: relative expression level).

DESCRIPTION OF THE PREFERRED EMBODIMENTS

Figure 1:
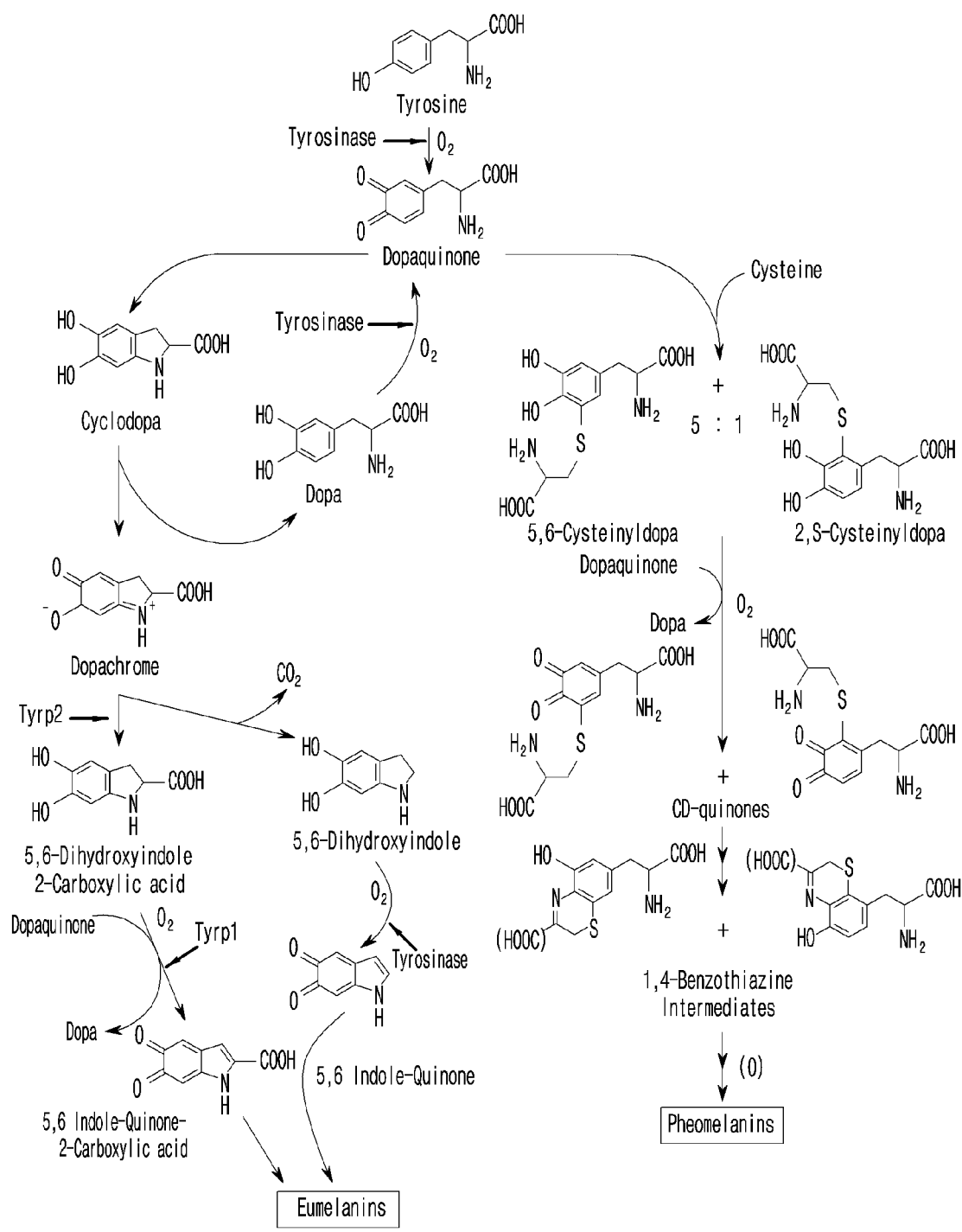
FIG. 1 is a schematic diagram illustrating the process of in vivo melanin biosynthesis.

Hereinafter, the present invention is described in detail.
In an aspect of the present invention, the present invention provides a compound represented by formula 1 below, an optical isomer thereof or a pharmaceutically acceptable salt thereof:

[Formula 1]

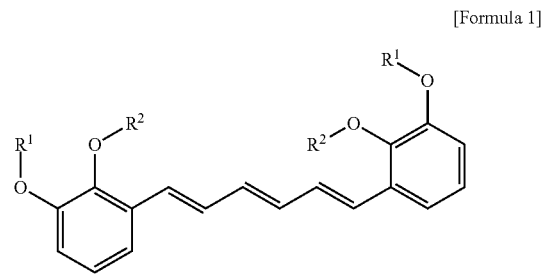

(In formula 1,
R¹ and R² are independently straight or branched $C_{1-6}$ alkyl).
The said R¹ and R² can be independently straight or branched $C_{1-3}$ alkyl.

Examples of the compounds represented by formula 1 according to the present invention include the compounds represented by the following formula 2:

[Formula 2]

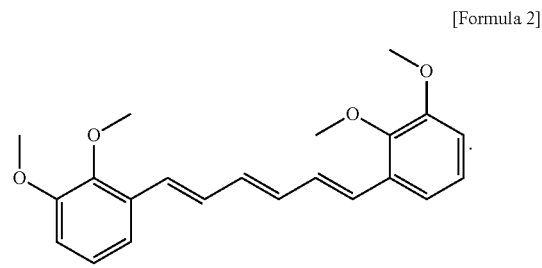 [SMILES: COc1cccc(/C=C/C=C/C=C/c2cccc(OC)c2OC)c1OC]

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

In addition, the present invention includes not only the compound represented by formula 1 but also a pharmaceutically acceptable salt thereof, and a solvate, an optical isomer, or a hydrate possibly produced from the same.

In another aspect of the present invention, the present invention provides a preparation method of a compound represented by formula 1 comprising a step of preparing a compound represented by formula 1 by reacting a compound represented by formula 3 with a compound represented by formula 4 as shown in reaction formula 1 below:

[Reaction Formula 1]

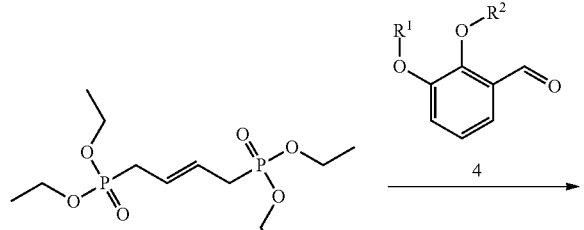

3

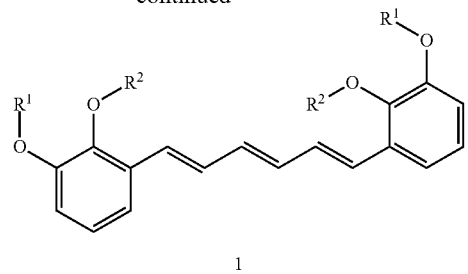

4

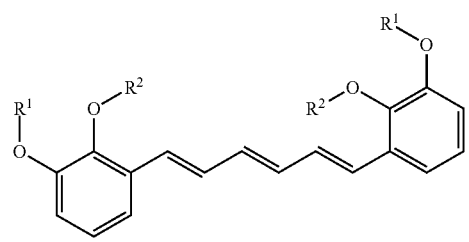

1

(In reaction formula 1,
$R^1$ and $R^2$ are as defined in formula 1 above).

Hereinafter, the preparation method shown in reaction formula 1 is described in more detail.

The preparation method shown in reaction formula is a method for preparing the compound represented by formula 1, which is only one example of the various synthesis methods of the compound represented by formula 1, but the preparation of the compound represented by formula 1 is not limited thereto.

Particularly, the preparation method above is a method to prepare the compound represented by formula 1 by reacting (E)-tetraethylbut-2-ene-1,4-diyldiphosphonate compound represented by formula 3 with benzaldehyde compound represented by formula 4 in order to form triene.

Specific examples thereof are illustrated in the following examples, and the examples are just examples for carrying out the preparation method above, and the reaction conditions are not limited to the examples.

In another aspect of the present invention, the present invention provides a cosmetic composition for skin whitening comprising a compound represented by formula 1 below or a pharmaceutically acceptable salt thereof as an active ingredient:

[Formula 1]

(In formula 1,
$R^1$ and $R^2$ are independently straight or branched $C_{1-6}$ alkyl).

To investigate the skin whitening effect of the compound represented by formula 1 according to the present invention, the inhibitory effect of the compound on the expression of tyrosinase, TRP 1 (tyrosinase-related protein 1), TRP 2 (tyrosinase-related protein 2) or MITF (microphthalmia-associated transcription factor) gene was measured.

Figure 2:
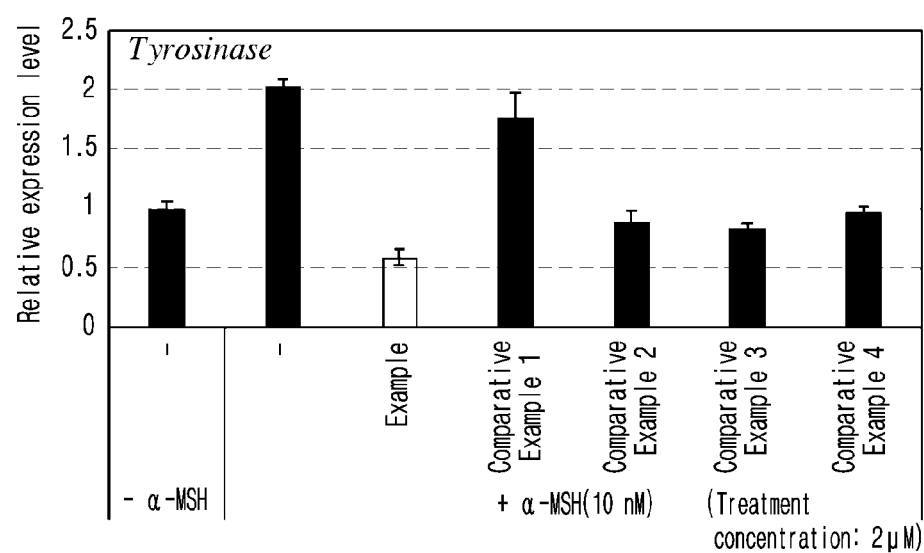
FIG. 2 is a graph illustrating the inhibitory effect of the compound of the present invention on tyrosinase gene expression, evaluated in Experimental Example 1 (vertical axis: relative expression level).
Figure 3:
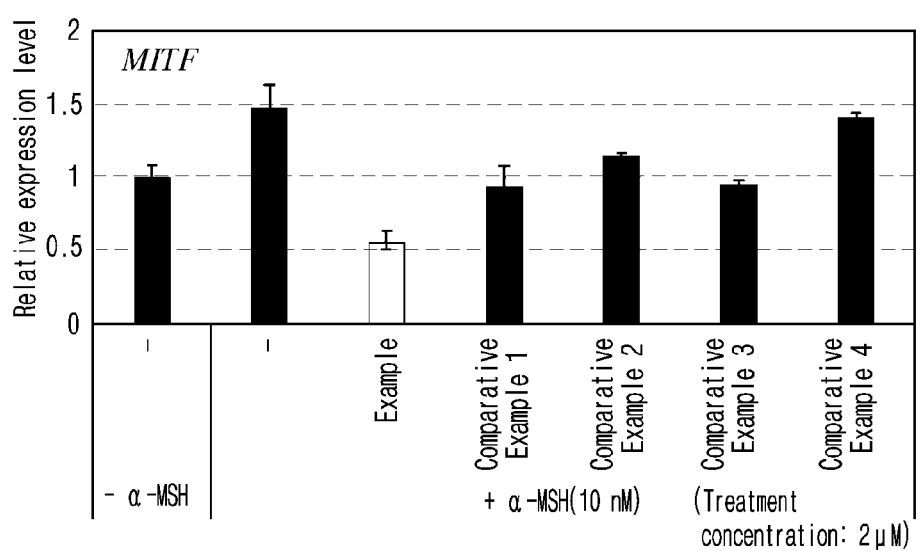
FIG. 3 is a graph illustrating the inhibitory effect of the compound of the present invention on MITF gene expression, evaluated in Experimental Example 2 (vertical axis: relative expression level).

As a result, the compound represented by formula 1 of the present invention was confirmed to have an excellent inhibitory effect on the expression of tyrosinase, TRP 1 (tyrosinase-related protein 1), TRP 2 (tyrosinase-related protein 2) or MITF (microphthalmia-associated transcription factor) gene which produces a precursor necessary for the generation of melanin even at a low concentration, indicating that the compound above had an excellent skin whitening effect (see Experimental Examples 1~3 and FIGS. 2~4).

The antioxidative effect of the compound represented by formula 1 of the present invention was measured. As a result, the compound represented by formula 1 of the present invention was confirmed to have an excellent antioxidative effect even at a low concentration (see Experimental Example 4 and FIG. 5).

The cytotoxicity of the compound represented by formula 1 of the present invention was measured. As a result, the compound represented by formula 1 of the present invention was confirmed to have a low cytotoxicity (see Experimental Example 5 and FIG. 6).

The inhibitory effect of the compound represented by formula 1 of the present invention on the production of melanin was measured. As a result, the compound represented by formula 1 of the present invention was confirmed to inhibit the production of melanin significantly even at a low concentration (see Experimental Example 6 and FIG. 7).

The inhibitory effect of the compound represented by formula 1 of the present invention on the activity of tyrosinase was measured. As a result, the compound represented by formula 1 of the present invention was confirmed to inhibit the activity of tyrosinase significantly even at a low concentration (see Experimental Example 7 and FIG. 8).

In the pharmaceutical composition according to the present invention, the compound represented by formula 1 or the pharmaceutically acceptable salt thereof can be administered orally or parenterally in various formulations at the time of clinical administration. More preferably, they can be parenteral formulations. The compound represented by formula 1 or the pharmaceutically acceptable salt thereof can be prepared for oral or parenteral administration by mixing with generally used diluents or excipients such as fillers, extenders, binders, wetting agents, disintegrating agents and surfactant. Solid formulations for oral administration are tablets, pills, powders, granules and capsules. These solid formulations are prepared by mixing the compound represented by formula 1 or the pharmaceutically acceptable salt thereof of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, and emulsions. Water insoluble excipients and suspensions can contain, in addition to the active compound or compounds, propylene glycol, polyethylene glycol, vegetable oil like olive oil, injectable ester like ethylolate, etc.

The present invention also provides a skin external application for skin whitening comprising the compound represented by formula 1 above as an active ingredient.

When the compound represented by formula 1 is used as a skin external application, it can include one or more additional supplements generally used in the field of skin science such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturing agent, essential oil, dye, pigment, hydrophilic or hydrophobic activator, lipid vesicle or other components generally used in the field of skin science. The said components can be included in the amounts generally used in the field of skin science.

When the compound represented by formula 1 is provided as a skin external application formulation, it can be ointments, patches, gels, creams or sprays, but not always limited thereto.

Preferably, the pharmaceutical composition of the present invention can be provided as a parenteral preparation. For example, the pharmaceutical composition of the present invention can be prepared as a skin external application by mixing homogeneously suitable pharmaceutically acceptable bases such as vaseline, stearyl alcohol and the like; suitable pharmaceutically acceptable surfactants such as polysorbate, sorbitan sesquioleate and the like; suitable pharmacologically acceptable moisturizing agents such as glycerin and the like; suitable pharmaceutically acceptable solvents; flavors; coloring agents; stabilizers; and viscosifying agents according to the conventional method for producing a skin external application.

When the compound represented by formula 1 of the present invention is used as a medicine, it can include one or more additional active ingredients which have the same or similar functions to the active ingredient. For example, a well known skin whitening component can be included. When an additional skin whitening component is included in the composition of the present invention, the skin whitening effect of the composition is expected to be increased.

In the case of adding additional ingredients, skin safety, easiness in formulation and stability of active ingredients are considered for combination use. In a preferred embodiment of the present invention, the composition can additionally include one or more ingredients selected from the group consisting of tyrosinase activity inhibitors such as kojic acid and arbutin, hydroquinone, vitamin-C (L-ascorbic acid), derivatives thereof and various plant extracts as known whitening components. The additional ingredient is preferably included in the composition at the concentration of 0.0001 weight %~10 weight % by the total composition. The concentration above can be adjusted according to requirements such as skin safety and easiness of formulation of the compound represented by formula 1, etc.

The pharmaceutical composition of the present invention can provide a preferable skin whitening effect when it contains an effective dose of the compound represented by formula 1. In this invention, the term 'effective dose' indicates the amount of a compound capable of exhibiting a skin whitening effect.

The effective dose of the compound represented by formula 1 included in the composition of the present invention can vary according to the form of the formulation, the method by which the compound is applied to the skin and the time on the skin. For example, when the composition of the present invention is formulated as a medicine, the concentration of the compound represented by formula 1 in the composition is higher than when it is formulated as a cosmetic composition to be applied on the skin. Therefore, the daily dose of the compound represented by formula 1 can be 0.1~100 mg/kg, preferably 30~80 mg/kg, and more preferably 50~60 mg/kg, and the administration frequency is preferably 1~6 times a day.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

In another aspect of the present invention, the present invention provides a cosmetic composition for skin whitening comprising a compound represented by formula 1 below, an optical isomer thereof or a pharmaceutically acceptable salt thereof as an active ingredient:

[Formula 1]

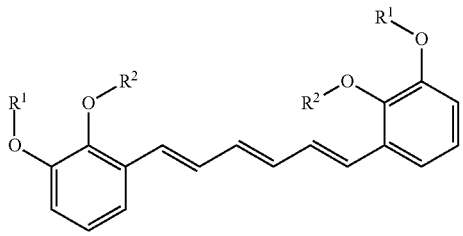

(In formula 1,
$R^1$ and $R^2$ are independently straight or branched $C_{1-6}$ alkyl).

To investigate the skin whitening effect of the compound represented by formula 1 according to the present invention, the inhibitory effect of the compound on the expression of tyrosinase, TRP 1 (tyrosinase-related protein 1), TRP 2 (tyrosinase-related protein 2) or MITF (microphthalmia-associated transcription factor) gene was measured. As a result, the compound represented by formula 1 according to the present invention was confirmed to have excellent skin whitening effect because it was excellent in inhibiting the expression of tyrosinase, TRP 1 (tyrosinase-related protein 1), TRP 2 (tyrosinase-related protein 2) or MITF (microphthalmia-associated transcription factor) gene producing a precursor of melanin biosynthesis even at a low concentration (see Experimental Examples 1~3 and FIGS. 2-4).

The antioxidative effect of the compound represented by formula 1 according to the present invention was also measured. As a result, the compound represented by formula 1 of the present was confirmed to have excellent antioxidative effect even at a low concentration (see Experimental Example 4 and FIG. 5).

The cytotoxicity of the compound represented by formula 1 according to the present invention was also measured. As a result, the compound represented by formula 1 of the present was confirmed to have low cytotoxicity (see Experimental Example 5 and FIG. 6).

The degree of inhibition of melanin synthesis by the compound represented by formula 1 according to the present invention was also measured. As a result, the compound represented by formula 1 of the present invention was confirmed to be excellent in inhibiting melanin synthesis even at a low concentration (see Experimental Example 6 and FIG. 7).

In addition, the inhibitory effect of the compound represented by formula 1 according to the present invention on the activity of tyrosinase was measured. As a result, the compound represented by formula 1 of the present was confirmed to have excellent inhibitory effect on the activity of tyrosinase even at a low concentration (see Experimental Example 7 and FIG. 8).

In the preparation of a composition for improving skin condition comprising a compound represented by formula 1 or a pharmaceutically acceptable salt thereof, the compound represented by formula 1 or the pharmaceutically acceptable salt thereof is preferably added to the composition for improving skin condition at the concentration of 3~30 weight part and preferably 5~20 weight part.

The cosmetic composition of the present invention can include, in addition to the compound represented by formula 1 or the pharmaceutically acceptable salt thereof of the present invention, a supplement generally used in the field of skin science such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturing agent, essential oil, dye, pigment, hydrophilic or hydrophobic activator, lipid vesicle or other components generally used in the field of skin science.

The said components can be included in the amounts generally used in the field of skin science.

The cosmetic composition of the present invention can be formulated in any form that can be accepted in the art, which is exemplified by solution, external ointment, cream, foam, nutritive lotion, skin, pack, makeup base, essence, soap, liquid detergent, bath preparation, sun screen cream, sun oil, suspension, emulsion, paste, gel, lotion, powder, surfactant-containing cleansing, oil, powdered foundation, emulsified foundation, wax foundation, patch and spray, but not always limited thereto.

In addition, the cosmetic composition of the present invention can additionally include one or more cosmetically acceptable carriers. As a general component, oil, water, surfactant, moisturizer, lower alcohol, thickener, chelating agent, coloring agent, antiseptic, perfume, and the like can be properly blended.

The cosmetically acceptable carrier to be included in the cosmetic composition of the present invention varies depending on the formulations. In the case that the cosmetic composition is formulated as ointment, paste, cream or gel, the proper carrier can be selected from the group consisting of animal oil, vegetable oil, wax, paraffin, starch, tragacanth, cellulose derivative, polyethylene glycol, silicone, bentonite, silica, talc, zinc oxide and mixtures thereof.

In the case that the cosmetic composition is formulated as powder or spray, the proper carrier can be selected from the group consisting of lactose, talc, silica, aluminum hydroxide, calcium silicate polyamide powder and mixtures thereof, and in particular if the composition of the present invention is formulated as spray, a propellant such as chlorofluorohydrocarbon, propane/butane or dimethyl ether can be additionally included.

In the case that the cosmetic composition is formulated as liquid or emulsion, the proper carrier can be selected from the group consisting of solvent, solubilizer and emulsifier, which is exemplified by water, ethanol, isopropanol, ethyl carbonate, ethyl acetate, benzyl alcohol, benzyl benzoate, propylene glycol, 1,3-butyl glycol oil, glycerol aliphatic ester, polyethylene glycol and fatty acid ester of sorbitan.

In the case that the cosmetic composition is formulated as suspension, the proper carrier can be selected from the group consisting of liquid diluent such as water, ethanol or propylene glycol, suspending agent such as ethoxylated isostearyl alcohol, polyoxyethylene sorbitol ester and polyoxyethylene sorbitan ester, microcrystalline cellulose, aluminum methahydroxide, bentonite, agar, and tragacanth.

In the case that the cosmetic composition is formulated as soap, the proper carrier can be selected from the group consisting of alkali metal salt of fatty acid, hemiester salt of fatty acid, protein hydrolizate of fatty acid, isethionate, lanolin derivative, aliphatic alcohol, vegetable oil, glycerol, and sugar.

The present invention also provides a method of skin whitening comprising a step of applying the compound represented by formula 1 to the skin of a subject. The subject includes, without limitation, mammals including rats, livestock, humans, and the like.

In another aspect of the present invention, the present invention provides an antioxidative composition comprising a compound represented by formula 1 below, an optical isomer thereof or a pharmaceutically acceptable salt thereof as an active ingredient:

[Formula 1]

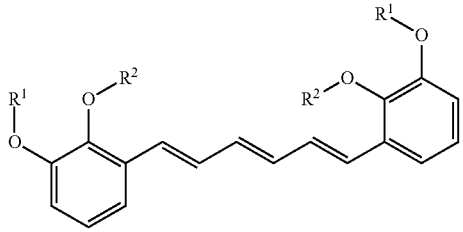

(In formula 1,
$R^1$ and $R^2$ are independently straight or branched $C_{1-6}$ alkyl).

The antioxidative effect of the compound represented by formula 1 according to the present invention was measured. As a result, the compound represented by formula 1 of the present was confirmed to have excellent antioxidative effect even at a low concentration (see Experimental Example 4 and FIG. 5).

The cytotoxicity of the compound represented by formula 1 according to the present invention was also measured. As a result, the compound represented by formula 1 of the present was confirmed to have low cytotoxicity (see Experimental Example 5 and FIG. 6).

In another aspect of the present invention, the present invention provides a health functional food for skin whitening comprising a compound represented by formula 1 below, an optical isomer thereof or a pharmaceutically acceptable salt thereof as an active ingredient:

[Formula 1]

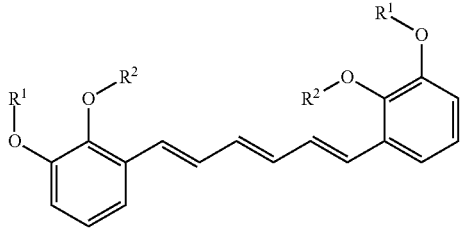

(In formula 1,
$R^1$ and $R^2$ are independently straight or branched $C_{1-6}$ alkyl).

In this description, the term 'health functional food' indicates the food prepared by adding the compound represented by formula 1 to food materials such as beverages, tea, spices, gums and snacks or the food prepared in such forms as capsule, powder and suspension with the compound which can bring a beneficiary effect on health. Unlike general medicines, their raw materials are food ingredients so that they have no side effects for a long term administration. The health functional food of the present invention obtained as the above can be taken daily, so that it is expected to bring excellent skin whitening effect, indicating that the health functional food is very useful.

The compound represented by formula 1 or the pharmaceutically acceptable salt thereof of the present invention can be added as it is or as mixed with other food components according to the conventional method. The mixing ratio of active ingredients can be regulated according to the purpose of use (prevention or amelioration). In general, to produce a health functional, the compound is added preferably by 0.1~90 weight part. However, if long term administration is required for health and hygiene or regulating health condition, the content can be lower than the above but higher content can be accepted as well since the compound has been proved to be very safe.

The composition for health beverages of the present invention can additionally include various flavors or natural carbohydrates, etc, like other beverages in addition to the compound. The natural carbohydrates above can be one of monosaccharides such as glucose and fructose, disaccharides such as maltose and sucrose, polysaccharides such as dextrin and cyclodextrin, and sugar alcohols such as xylytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 g of the composition of the present invention.

In addition to the ingredients mentioned above, the compound represented by formula 1 or the pharmaceutically acceptable salt thereof of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 or the pharmaceutically acceptable salt thereof of the present invention can also include natural fruit juice, fruit beverages and/or fruit flesh addable to vegetable beverages.

The compound represented by formula 1 according to the present invention is excellent in inhibiting the expression of tyrosinase, TRP 1 (tyrosinase-related protein 1), TRP 2 (tyrosinase-related protein 2) or MITF (microphthalmia-associated transcription factor) gene which produces a precursor necessary for the generation of melanin even at a low concentration and is also excellent in suppressing the activity of tyrosinase, so that it eventually inhibits the production of melanin. In addition, the cell survival rate is maintained at about 80% even when the concentration of the compound according to the present invention is increased, that is, the compound has a significantly low cytotoxicity indicating that the compound is safe, and has low side effects and excellent antioxidative effects. Therefore, the compound of the present invention can be effectively used as a pharmaceutical composition for skin whitening, a cosmetic composition for skin whitening, a health functional food for skin whitening, and an antioxidative composition.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of (1E,3E,5E)-1,6-bis(2,3-dimethoxyphenyl)hexa-1,3,5-triene

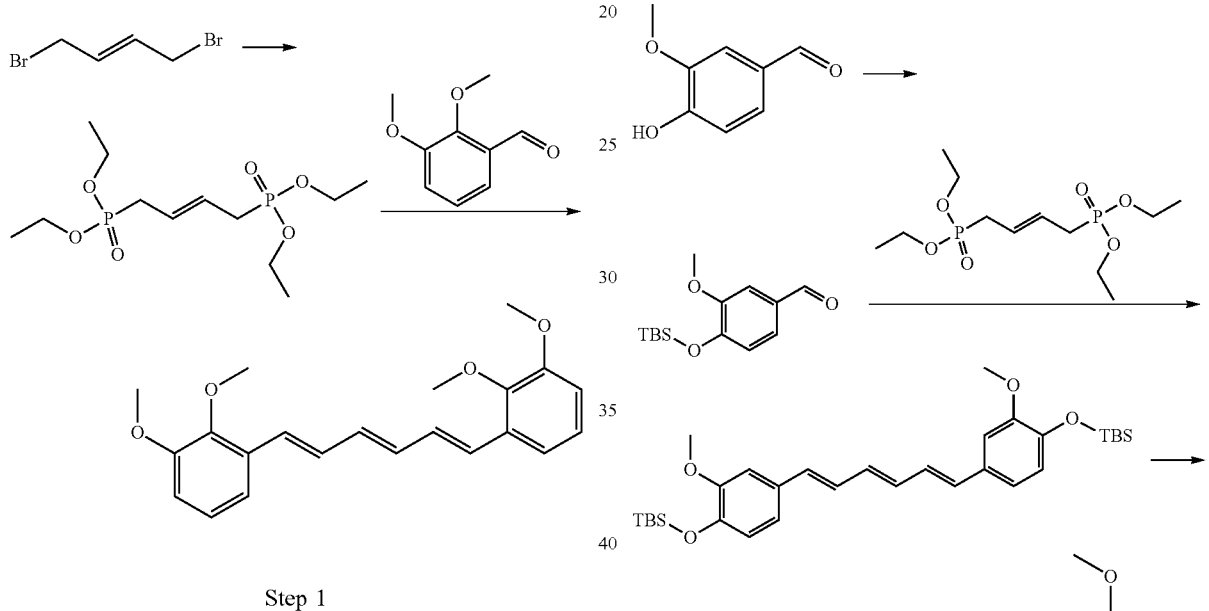

Step 1

Preparation of (E)-tetraethyl but-2-ene-1,4-diylphosphonate

Triethylphosphite (4 mL) solution containing trans-1,4-dibromobutene (2.0 g, 9.35 mmol) was refluxed for 5 hours. The reaction solution was cooled down and the solvent was eliminated. The residue was purified by silica gel column chromatography (eluent=hexane/ethylacetate=1/3) and as a result, (E)-tetraethyl but-2-ene-1,4-diyldiphosphonate (3.12 g, 99%) was obtained.

$^1$H NMR (300 MHz, DMSO) δ 5.58-5.46 (m, 2H), 4.08-3.91 (m, 8H), 2.65 (ddd, J=17.5, 10.0, 7.2 Hz, 4H), 1.21 (q, J=7.1 Hz, 12H).

Step 2

Preparation of (1E,3E,5E)-1,6-bis(2,3-dimethoxyphenyl)hexa-1,3,5-triene

Tetrahydrofuran (THF) solution containing (E)-tetraethyl but-2-ene-1,4-diyldiphosphonate (0.5 g, 1.52 mmol, 0.6 eq) obtained in step 1 above and 2,3-dimethoxybenzaldehyde (1 eq) was added to THF solution in which NaH (1.5 eq) was suspended. The reaction mixture was stirred at room temperature for 2~5 hours, followed by extraction with methylene chloride and NH$_4$Cl aqueous solution. The organic layer was dried and filtered, and the solvent was evaporated. The residue was purified by silica gel column chromatography (eluent=hexane/ethylacetate=2/1) and as a result, a target compound (0.30 g, yield 56%) was obtained.

$^1$H NMR (300 MHz, DMSO) δ 7.21-7.17 (m, 2H), 7.11-6.97 (m, 3H), 7.04-6.81 (m, 5H), 6.64-6.57 (m, 2H), 3.93 (s, 6H), 3.89 (s, 6H).

COMPARATIVE EXAMPLE 1

Preparation of 4,4'-((1E,3E,5E)-hexa-1,3,5-triene-1,6-diyl)bis(2-methoxyphenol)

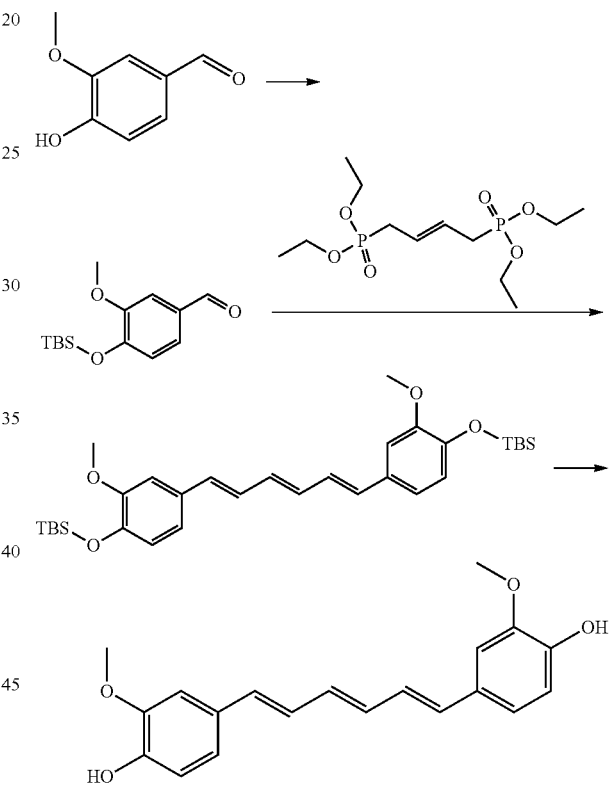

Step 1

Preparation of 4-(tert-butyldimethylsilyloxy)-3-methoxybenzaldehyde

Tert-butyldimethylsilyl chloride (1.25 eq) was added to THF solution containing 4-hydroxy-3-methoxybenzaldehyde (1.0 eq) and imidazole (2.5 eq). The reaction mixture was stirred at room temperature, followed by extraction with methylene chloride and NH$_4$Cl aqueous solution. The organic layer was dried and filtered, and the solvent was evaporated. The residue was purified by silica gel column chromatography (eluent=hexane/ethylacetate=50/1) and as a result, a target compound was obtained.

Step 2

Preparation of (1E,3E,5E)-1,6-bis(4-(tert-butyldimethylsilyloxy)-3-methoxyphenyl)hexa-1,3,5-triene (1E,3E,5E)-1,6-bis(4-(tert-butyldimethylsilyloxy)-3-methoxyphenyl)hexa-1,3,5-triene was obtained (yield 55%) by the same manner as described in step 2 of Example 1 except 4-(tert-butyldimethylsilyloxy)-3-methoxybenzaldehyde obtained in step 1 above was used instead of 2-methoxybenzaldehyde.

Step 3

Preparation of 4,4'-((1E,3E,5E)-hexa-1,3,5-triene-1,6-diyl)bis(2-methoxyphenol)

Tetra-n-butylammonium fluoride (TBAF, 2.05 eq) was added to THF solution containing (1E,3E,5E)-1,6-bis(4-(tert-butyldimethylsilyloxy)-3-methoxyphenyl)hexa-1,3,5-triene (0.050 g, 0.0904 mmol), followed by stirring at room temperature for 5 hours. Then, THF was eliminated in vacuum condition. The residue was diluted in ethyl acetate (100 mL). The ethyl acetate layer was washed with water (50 ml*2) and the organic layer was dried over anhydrous sodium sulfate. The solvent was eliminated in vacuum condition, followed by silica gel column chromatography (10% EA/Hx) for purification. As a result, a target compound was obtained (yield 99%).

$^1$H NMR (500 MHz, CDCl$_3$) δ 6.96 (d, J=7.6 Hz, 4H), 6.90 (d, J=8.2 Hz, 2H), 6.80-6.73 (m, 2H), 6.55 (s, 1H), 6.51 (s, 1H), 6.49 (dd, J=7.0, 3.0 Hz, 2H), 5.66 (s, 2H), 3.96 (s, 6H).

COMPARATIVE EXAMPLE 2

Preparation of (E)-4-((4-methoxyphenylimino)methyl)benzene-1,3-diol

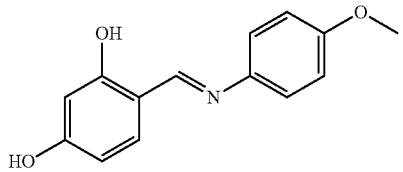 [SMILES: COc1ccc(/N=C/c2ccc(O)cc2O)cc1]

2,4-Dihydroxybenzaldehyde (200 mg) and p-anisidine (1.0 eq.) were added to ethyl alcohol (4 mL) solvent. The mixture was stirred at room temperature for 30 minutes. Water was added thereto, the reaction mixture was maintained at 0° C. The resulting precipitate was filtered and washed with water. As a result, a target compound was obtained.

$^1$H NMR (300 MHz, DMSO-d$_6$) δ 10.18 (br s, 1H), 8.77 (s, 1H), 7.41-7.31 (m, 3H), 7.04-6.98 (m, 2H), 6.39 (dd, J=9.0, 3.0 Hz, 1H), 6.29 (d, J=3.0 Hz, 1H), 3.78 (s, 3H).

COMPARATIVE EXAMPLE 3

Preparation of 4,4'-((1E,3E,5E)-hexa-1,3,5-triene-1,6-diyl)diphenol

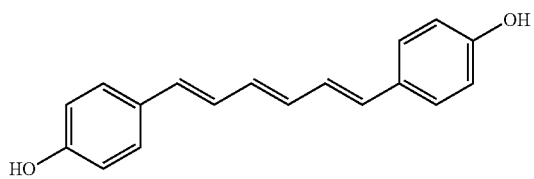 [SMILES: Oc1ccc(/C=C/C=C/C=C/c2ccc(O)cc2)cc1]

(E)-tetraethyl but-2-ene-1,4-diyldiphosphonate solution (0.6 eq.) dissolved in THF solvent and TBS(tert-butyldimethylsil)-protected 4-hydroxybenzaldehyde solution (1.0 eq.) dissolved in THF solvent were added to NaH (1.5 eq.) suspension dissolved in THF (tetrahydrofuran), followed by stirring at room temperature for 2~5 hours. The reaction mixture was distributed between methylene chloride and NH$_4$Cl aqueous solution. The organic layer was dried, filtered and evaporated. The residue was purified by silica gel column chromatography using hexane and ethyl acetate (EtOAc) (2:1). As a result, triene was obtained. 12 N HCl was added to triene solution in THF and methanol (4:1) solvent. The reaction mixture was stirred at room temperature for overnight. The reaction mixture was distributed between ethyl acetate (EtOAc) and water. The organic layer was washed with NaHCO$_3$ aqueous solution. The organic layer was dried, filtered and evaporated. The residue was purified by silica gel column chromatography and as a result, a target compound was obtained.

$^1$H NMR (300 MHz, DMSO-d$_6$) δ 9.59 (br s, 2H), 7.31 (d, J=9 Hz, 4H), 6.83-6.72 (m, 6H), 6.54-6.44 (m, 4H).

COMPARATIVE EXAMPLE 4

Preparation of 5,5'-((1E,3E,5E)-hexa-1,3,5-triene-1,6-diyl)bis(2-methoxyphenol)

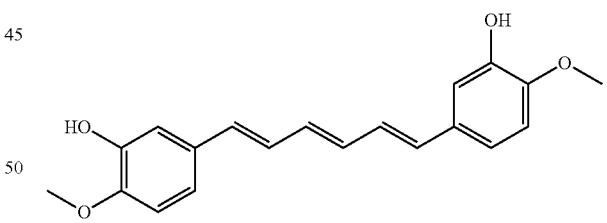

(E)-tetraethyl but-2-ene-1,4-diyldiphosphonate solution (0.6 eq.) dissolved in THF solvent and TBS(tert-butyldimethylsil)-protected 3-hydroxy-4-methoxy benzaldehyde solution (1.0 eq.) dissolved in THF solvent were added to NaH (1.5 eq.) suspension dissolved in THF (tetrahydrofuran), followed by stirring at room temperature for 5 hours. The reaction mixture was distributed between methylene chloride and NH$_4$Cl aqueous solution. The organic layer was dried, filtered and evaporated. The residue was purified by silica gel column chromatography using hexane and ethyl acetate (EtOAc) (2:1). As a result, triene was obtained. 12 N HCl was added to triene solution in THF and methanol (4:1) solvent. The reaction mixture was stirred at room temperature for overnight. The reaction mixture was distributed between ethyl acetate (EtOAc) and water. The organic layer was washed with NaHCO$_3$ aqueous solution. The organic layer was dried, filtered and evaporated. The residue was purified by silica gel column chromatography and as a result, a target compound was obtained.

$^1$H NMR (300 MHz, DMSO-d$_6$) δ 8.97 (br s, 2H), 7.42-7.32 (m, 1H), 7.12-6.78 (m, 7H), 6.55-6.47 (m, 2H), 6.26-6.12 (m, 2H), 3.85 (dd, J=9.0, 3.0 Hz, 6H).

EXPERIMENTAL EXAMPLE 1

Evaluation of Inhibition of Tyrosinase Gene Expression

The following experiment was performed to evaluate the tyrosinase gene expression inhibition by the compound of example of the present invention.

B16F10 melanoma cells were distributed in a 6-well plate, to which α-MSH (10 nM) (melanin synthesis inducing substance, alpha-melanocyte-stimulating hormone) and the compounds of example and comparative examples 1~4 were treated at the concentration of 2 μM each, followed by exposure-culture for 72 hours. Then, the cells were harvested and total RNA of the cells was extracted using RNeasy mini kit (Qiagen). CDNA was synthesized by using M-MLV reverse transcriptase, 5X first-strand butter, dNTP mix and oligo(dT) primer (Thermo Fisher Scientific). The cDNA product, the primers of each gene and LightCycler® MultiplexMasters (Roche) were mixed, followed by SYBR Green-based real-time PCR using LightCycler® NanoInstrument (Roche). To relatively evaluate the level of tyrosinase mRNA expression, the expression was corrected based on the level of β-actin mRNA expression. The PCR conditions for gene amplification are as follows.

Denaturation: 95° C., 10 seconds
Annealing: melting point of each primer, 10 seconds
Extension/Detection: 72° C., 20 seconds
Total cycle number: 45 cycles Information on the primers used for the amplification of tyrosinase gene expression and information on the primers for β-actin used as a correction gene are as follows.

```
                                         (SEQ ID NO. 1)
   bACT-F: ACTATTGGCAACGAGCGGTT (SEQ ID NO. 2)
   bACT-R: ATGGATGCCACAGGATTCCA (SEQ ID NO. 3)
   TYR-F:  CCTCCTGGCAGATCATTTGT (SEQ ID NO. 4)
   TYR-R:  GGCAAATCCTTCCAGTGTGT
```

FIG. 2 is a graph illustrating the inhibitory effect of the compound of the present invention on tyrosinase gene expression, evaluated in Experimental Example 1 (vertical axis: relative expression level).

As shown in FIG. 2, the compound of example of the present invention was excellent in inhibiting tyrosinase gene expression. On the other hand, the group treated with the compound of comparative example 1 showed similar level of gene expression as the untreated group, indicating that the compound of comparative example 1 hardly had inhibitory effect on the expression of tyrosinase gene. The compounds of comparative examples 2~4 also displayed lower inhibitory effect than the compound of example of the present invention, indicating that the compound of example of the present invention was most excellent in inhibiting tyrosinase gene expression.

EXPERIMENTAL EXAMPLE 2

Evaluation of Inhibition of MITF (Microphthalmia-Associated Transcription Factor) Gene Expression The following experiment was performed to evaluate the MITF (microphthalmia-associated transcription factor) gene expression inhibition by the compound of example of the present invention.

Evaluation of MITF gene expression was performed by the same manner as described in the evaluation of tyrosinase gene expression in experimental example 1. Information on the primers used for the amplification of MITF gene expression is as follows.

```
                                         (SEQ ID NO. 5)
   MITE-F: AGGACCTTGAAAACCGACAG (SEQ ID NO. 6)
   MITF-R: GTGGATGGGATAAGGGAAAG
```

FIG. 3 is a graph illustrating the inhibitory effect of the compound of the present invention on MITF gene expression, evaluated in Experimental Example 2 (vertical axis: relative expression level)

As shown in FIG. 3, the compound of example of the present invention was excellent in inhibiting MITF gene expression. On the other hand, the groups treated with the compounds of comparative examples 1~4 showed higher level of MITF gene expression (2~3 times) than the group treated with the compound of example of the present invention, indicating that the compounds of comparative examples 1~4 hardly had inhibitory effect on the expression of MITF gene.

EXPERIMENTAL EXAMPLE 3

Evaluation of Inhibition of TRP 1 (Tyrosinase-Related Protein 1) and TRP 2 (Tyrosinase-Related Protein 2) Gene Expression The following experiment was performed to evaluate the TRP 1 (tyrosinase-related protein 1) and TRP 2 (tyrosinase-related protein 2) gene expression inhibition by the compound of example of the present invention.

Evaluation of TRP 1 and TRP 2 gene expression was performed by the same manner as described in the evaluation of tyrosinase gene expression. Information on the primers used for the amplification of TRP 1 and TRP 2 gene expression is as follows.

```
                                         (SEQ ID NO. 7)
   TRP1-F, CTTGGAGGTCCGTGTATTTG (SEQ ID NO. 8)
   TRP1-R, GACCGCATCAGTGAAAGTGT (SEQ ID NO. 9)
   TRP2-F, TACCATCTGTTGTGGCTGGA (SEQ ID NO. 10)
   TRP2-R, CAAGCTGTCGCACACAATCT
```

Figure 4A:
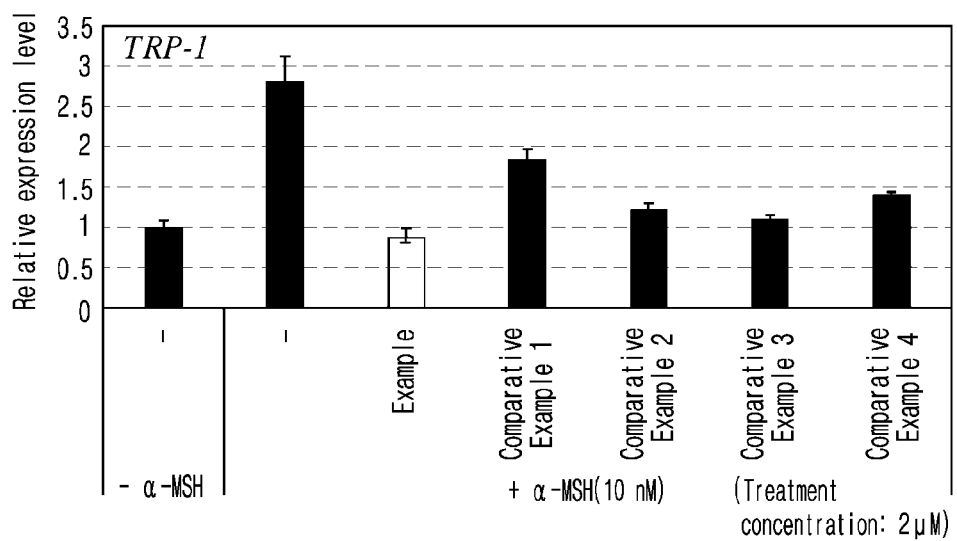
FIG. 4a: TRP 1.
Figure 4B:
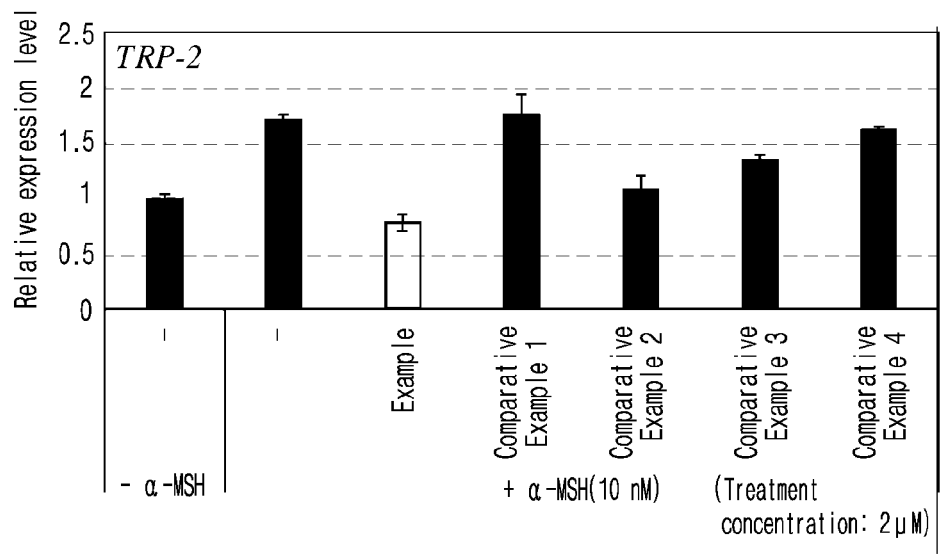
FIG. 4b: TRP 2

FIG. 4 is a set of graphs illustrating the inhibitory effect of the compound of the present invention on TRP 1 and TRP 2 gene expression, evaluated in Experimental Example 3 (vertical axis: relative expression level). FIG. 4a: TRP 1, FIG. 4b: TRP 2

As shown in FIG. 4, the compound of example of the present invention was excellent in inhibiting TRP1 and TRP2 gene expression. On the other hand, the groups treated with the compounds of comparative examples 1~4 showed higher level of TRP1 and TRP2 gene expression (1.2~2 times) than the group treated with the compound of example of the present invention. In particular, the groups treated with the compounds of comparative examples 1, 3 and 4 showed similar level of TRP 2 gene expression as the untreated group, indicating that the compounds of comparative examples had significantly low inhibitory effect on the expression of TRP 1 and TRP 2 gene.

EXPERIMENTAL EXAMPLE 4

Evaluation of Antioxidative Effect

The following experiment was performed to evaluate antioxidative effect of the compound of example of the present invention.

The antioxidative effect was evaluated by 2,2-diphenyl-1-picrylhydrazyl (DPPH) radical scavenging activity test.

Dimethyl sulfoxide (DMSO), vitamin C and the compounds of example and comparative examples 1~4 were added to a 96-well plate at each designated concentration, and 200 μL of 200 μM DPPH methanolic solution was added to each well. The plate was shaken gently to mix them all, followed by reaction at 37° C. for 30 minutes. Then, $OD_{515}$ was measured. DMSO was used as the control for the measurement of antioxidative effect and vitamin C was used as the positive control for the measurement of antioxidative effect.

Figure 5:
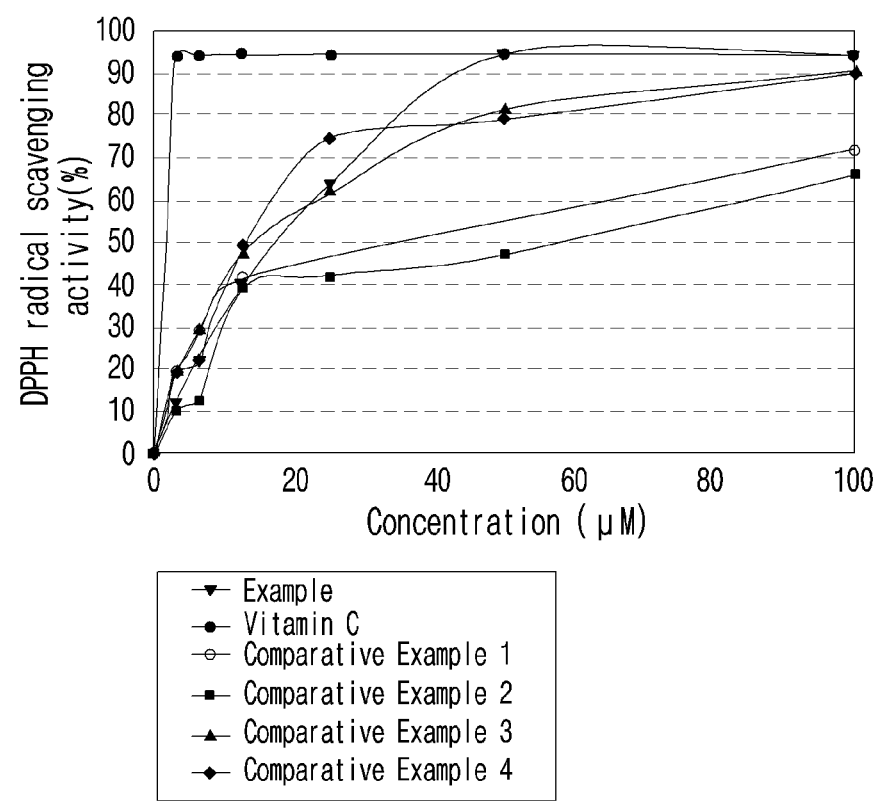
FIG. 5 is a graph illustrating the antioxidative effect of the compound of the present invention, evaluated in Experimental Example 4 (vertical axis: radical scavenging activity, horizontal axis: concentration).

FIG. 5 is a graph illustrating the antioxidative effect of the compound of the present invention, evaluated in Experimental Example 4 (vertical axis: radical scavenging activity, horizontal axis: concentration).

As shown in FIG. 5, the compound of example of the present invention displayed excellent antioxidative effect at the concentration of about 25 μM, compared with the compounds of comparative examples 1~3. Compared with the compounds of comparative examples 1~4, the compound of example of the present invention displayed excellent antioxidative effect at the concentration of 40 μM.

EXPERIMENTAL EXAMPLE 5

Evaluation of Cytotoxicity

The following experiment was performed to evaluate cytotoxicity of the compound of example of the present invention.

B16F10 melanoma cells were distributed in a 96-well plate at the density of $2 \times 10^3$ cells/well. The cells were cultured in DMEM supplemented with 10% fetal bovine serum (FBS) at 37° C. in 5% $CO_2$ for 24 hours. The cells were exposed on the compounds of example and comparative examples 1~4 at the set concentration each for 48 hours. MTT assay was performed to evaluate cytotoxicity. To perform MTT assay, MTT solution was added to the cells, followed by reaction for 2 hours. Then, DMSO was added thereto to dissolve formazan crystals, followed by measurement of $OD_{570}$.

Figure 6:
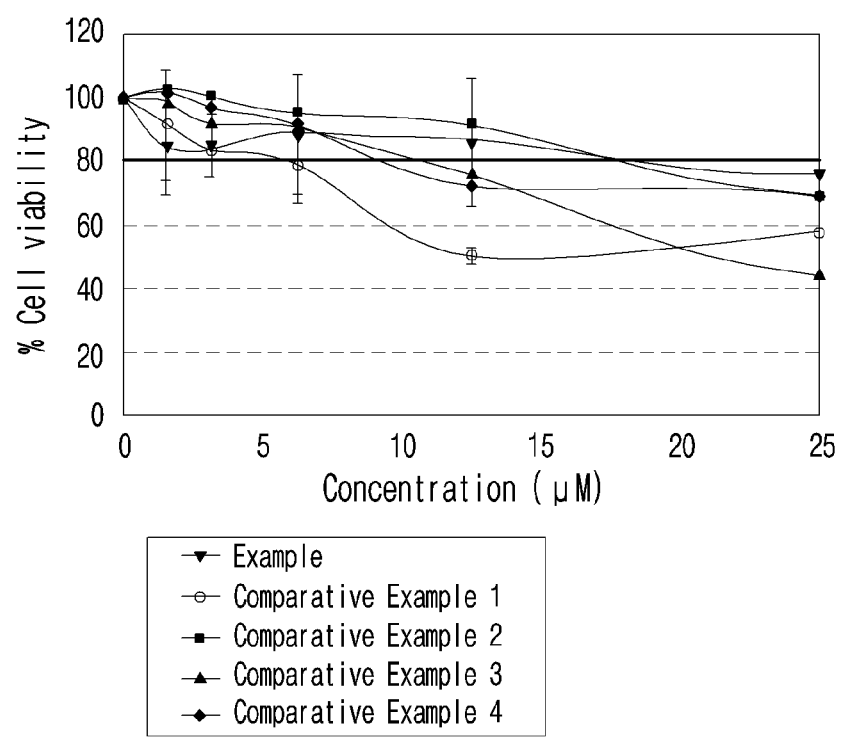
FIG. 6 is a graph illustrating the cytotoxicity of the compound of the present invention, evaluated in Experimental Example 5 (vertical axis: cell viability).

FIG. 6 is a graph illustrating the cytotoxicity of the compound of the present invention, evaluated in Experimental Example 5 (vertical axis: cell viability).

As shown in FIG. 6, despite increasing the concentration of the compound of example of the present invention from 5 μM to 15 μM, the cell survival rate was maintained at 80% or more. That is, the compound of the present invention exhibited excellent skin whitening effect and at the same time displayed no cytotoxicity, so that it had both pharmacological effect and safety, and has an effect of reducing side effects caused by toxicity.

On the other hand, the compounds of comparative examples 1~4 displayed lower skin whitening effect than the compound of example of the present invention. In particular, the compounds of comparative examples 1, 3 and 4 demonstrated strong cytotoxicity at the concentration of 10 μM or more, indicating that the safety was low and thereby side effects were predicted.

EXPERIMENTAL EXAMPLE 6

Evaluation of Melanin Synthesis Inhibition

The following experiment was performed to evaluate the inhibitory effect of the compound of example of the present invention on melanin synthesis.

B16F10 melanoma cells were distributed in a 96-well plate at the density of $3 \times 10^5$ cells/well. The cells were cultured in DMEM supplemented with 10% FBS at 37° C. in 5% $CO_2$ for 24 hours. The cells were treated with α-MSH (10 nM) and the compounds of example and comparative examples 1~4 at the concentration of 2 μM each, followed by culture for 72 hours. The cells were harvested, followed by dissolving in 1 N NaOH by heating at 80° C. for 20 minutes. Then, $OD_{490}$ was measured. The melanin synthesis inhibition rate was calculated as follows.

Melanin inhibition rate (%)=[(C−S)/C]×100

C: OD when α-MSH alone was treated.

S: OD when each sample was treated.

Figure 7:
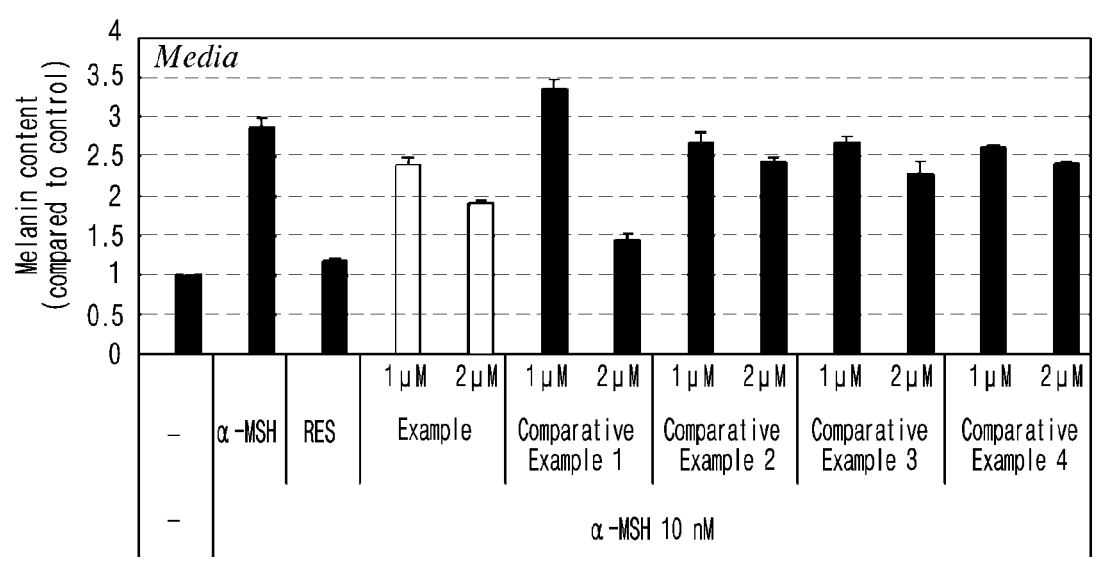
FIG. 7 is a set of graphs illustrating the inhibitory effect of the compound of the present invention on the production of melanin, evaluated in Experimental Example 6 (vertical axis: melanin content (compared to control), Media: cell culture fluid, α-MSH: alpha-melanocyte-stimulating hormone (10 nM), RES: melanin synthesis inhibitor (Resveratrol, 10 μM)).

FIG. 7 is a set of graphs illustrating the inhibitory effect of the compound of the present invention on the production of melanin, evaluated in Experimental Example 6 (vertical axis: melanin content (compared to control), Media: cell culture fluid, α-MSH: alpha-melanocyte-stimulating hormone (10 nM), RES: melanin synthesis inhibitor (Resveratrol, 10 μM)).

As shown in FIG. 7, the compound of example of the present invention was confirmed to have inhibitory effect on melanin synthesis. Particularly, when the cells were treated with the compound of example of the present invention at the concentration of 1 μM, the melanin content was lower in both media and cells than when the cells were treated with the compounds of comparative examples 1~4. In particular, the melanin content in the cells treated with the compound of example was significantly lower than the cells treated with the compounds of comparative examples, indicating that the compound of the present invention had excellent inhibitory effect on melanin synthesis.

EXPERIMENTAL EXAMPLE 7

Evaluation of Tyrosinase Activity Inhibition

Figure 8:
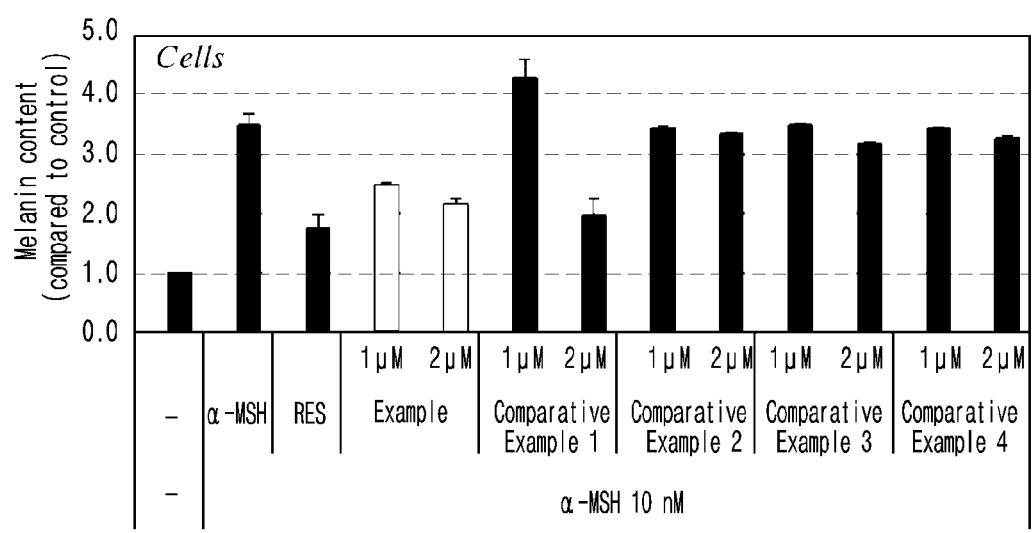
FIG. 8 is a graph illustrating the inhibitory effect of the compound of the present invention on the activity of tyrosinase, evaluated in Experimental Example 7 (vertical axis: tyrosinase activity (% of control), horizontal axis: concentration).
Figure 9:
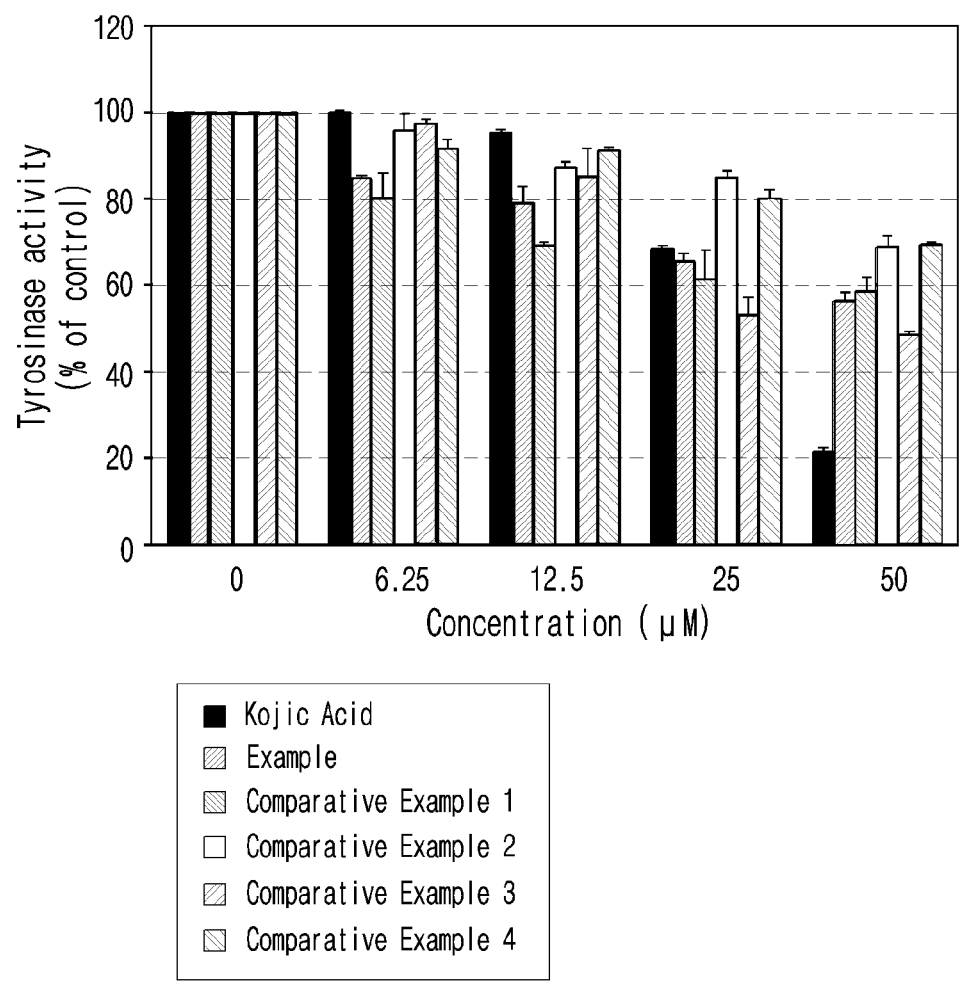

The following experiment was performed to evaluate the inhibitory effect of the compound of example of the present invention on tyrosinase activity and the results are shown in FIG. 8.

Samples were dissolved in an organic solvent such as ethanol, which were diluted in a proper buffer such as 100 mM phosphate buffer (pH 7.0). Those samples diluted at a proper concentration in order to inhibit the activity to DOPA oxidation reaction were used as the sample solutions for the experiment. 850 μL of 100 mM phosphate buffer (pH 7.0), 50 μL of the sample solution and 50 μL of mushroom tyrosinase (2000 U/ml) were loaded in a test tube in that order, followed by reaction at 37° C. for 5 minutes. 50 μL of 0.06 mM L-DOPA (L-3,4-dihydroxyphenylalanine) solution was added thereto, and then $OD_{475}$ was measured using a microplate reader. After reacting the solution at 37° C. for 15 minutes, $OD_{475}$ was measured again. DMSO was used as the control and Kojic acid was used for the positive control.

Tyrosinase activity inhibition rate (%)=[(A-B)/A]×100

A: difference of OD in the control group (OD after the reaction—OD before the reaction)

B: difference of OD in the experimental group (OD after the reaction—OD before the reaction)

FIG. 8 is a graph illustrating the inhibitory effect of the compound of the present invention on the activity of tyrosinase, evaluated in Experimental Example 7 (vertical axis: tyrosinase activity (% of control), horizontal axis: concentration).

As shown in FIG. 8, the compound of example of the present invention was confirmed to have inhibitory effect on tyrosinase activity. Particularly, when the compound of example of the present invention was treated to the cells at the concentration of 6.25 μM, the tyrosinase activity therein was reduced approximately 20%. Compared with that the compounds of comparative examples 2 and 3 treated to the cells at an equal concentration to the above did not show inhibitory effect on tyrosinase activity, the compound of example of the present invention was confirmed to have excellent inhibitory effect on tyrosinase activity.

Therefore, the compound represented by formula 1 of the present invention is excellent in inhibiting the expression of tyrosinase, TRP 1 (tyrosinase-related protein 1), TRP 2 (tyrosinase-related protein 2) or MITF (microphthalmia-associated transcription factor) gene which produces a precursor necessary for the generation of melanin even at a low concentration and is also excellent in suppressing the activity of tyrosinase, so that it eventually inhibits the production of melanin. In addition, the cell survival rate is maintained at about 80% even when the concentration of the compound according to the present invention is increased, that is, the compound has a significantly low cytotoxicity indicating that the compound is safe, and has low side effects and excellent antioxidative effects. Therefore, the compound of the present invention can be effectively used as a pharmaceutical composition for skin whitening, a cosmetic composition for skin whitening, a health functional food for skin whitening, and an antioxidative composition.

MANUFACTURING EXAMPLE 1

Preparation of Powders

| | |
|---|---|
| Compound represented by formula 1 | 2 g |
| Lactose | 1 g |

Powders were prepared by mixing all the above components, which were filled in airtight packs according to the conventional method for preparing powders.

MANUFACTURING EXAMPLE 2

Preparation of Tablets

| | |
|---|---|
| Compound represented by formula 1 | 100 mg |
| Corn starch | 100 mg |
| Lactose | 100 mg |
| Magnesium stearate | 2 mg |

Tablets were prepared by mixing all the above components by the conventional method for preparing tablets.

MANUFACTURING EXAMPLE 3

Preparation of Capsules

| | |
|---|---|
| Compound represented by formula 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

MANUFACTURING EXAMPLE 4

Preparation of Injectable Solutions

| | |
|---|---|
| Compound represented by formula 1 | 100 mg |
| Mannitol | 180 mg |
| $Na_2HPO_4 \cdot 2H_2O$ | 26 mg |
| Distilled water | 2974 mg |

Injectable solutions were prepared by incorporating all the above components in the prescribed amounts according to the conventional method for preparing injectable solutions.

MANUFACTURING EXAMPLE 5

Preparation of Ointments

| | |
|---|---|
| Compound represented by formula 1 | 5 g |
| Cetyl Palmitate | 20 g |
| Cetanol | 40 g |
| Stearyl Alcohol | 40 g |
| Myristanisopropyl | 80 g |
| Polysorbate | 60 g |
| Propyl p-hydroxybenzoate | 1 g |
| Methyl p-hydroxybenzoate | 1 g |

Phosphoric acid and purified water proper amount ointments were prepared by incorporating all the above components in the prescribed amounts according to the conventional method for preparing ointments.

MANUFACTURING EXAMPLE 6

Preparation of Health Functional Food

| | |
|---|---|
| Compound represented by formula 1 | 500 ng |
| Vitamin complex | proper amount |
| Vitamin A acetate | 70 mg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 mg |
| Vitamin C | 10 mg |
| Biotin | 10 mg |
| Nicotinic acid amide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health functional food. However, the composition rate can be adjusted. The constituents were mixed according to the conventional method for preparing health functional food and then the composition for health functional food was prepared according to the conventional method.

MANUFACTURING EXAMPLE 7

Preparation of Health Beverages

| | |
|---|---|
| Compound represented by formula 1 | 500 ng |
| Citric acid 삭 | 1000 mg |
| Oligosaccharide | 100 g |
| Maesil (*Prunus mume*) extract | 2 g |
| Taurine | 1 g |
| Purified water | 900 ml |

The above constituents were mixed according to the conventional method for preparing health beverages. The mixture was heated at 85° C. for 1 hour with stirring and then filtered. The filtrate was loaded in sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

MANUFACTURING EXAMPLE 8

Preparation of Composition For Skin Beauty

8-1 Preparation of Cream

| | |
|---|---|
| Compound represented by formula 1 | 4.6 weight part |
| Setearylalcohol | 2.8 weight part |
| Bees Wax | 2.6 weight part |
| Stearic acid | 1.4 weight part |
| Lipophilic glycerylstearate | 2 weight part |
| PEG-100 stearate | 1 weight part |
| Sesquioleic acid sorbital | 1.4 weight part |
| Jojoba oil | 4 weight part |
| Squalan | 3.8 weight part |
| Polysorbate 60 | 1.1 weight part |
| Macadamia oil | 2 weight part |
| Tocopherol acetate | 0.2 weight part |
| Methyl polysiloxane | 0.4 weight part |
| Ethylparaben | 0.1 weight part |
| Propylparaben | 0.1 weight part |
| Euxyl K-400 | 0.1 weight part |
| 1,3-butylene glycol | 7 weight part |
| Methylparaben | 0.05 weight part |
| Glycerin | 6 weight part |
| d-panthenol | 0.2 weight part |
| Triethanolamine | 0.2 weight part |
| pt 41891 | 0.2 weight part |
| p-H$_2$O | 46.05 weight part |

8-2 Preparation of Lotion

| | |
|---|---|
| Compound represented by formula 1 | 3.5 weight part |
| Setearylalcohol | 1.6 weight part |
| Stearic acid | 1.4 weight part |
| Lipophilic glycerylstearate | 1.8 weight part |
| PEG-100 stearate | 2.6 weight part |
| Sesquioleic acid sorbital | 0.6 weight part |
| Squalene | 4.8 weight part |
| Macadamia oil | 2 weight part |
| Jojoba oil | 2 weight part |
| Tocopherol acetate | 0.4 weight part |
| Methyl polysiloxane | 0.2 weight part |
| Ethylparaben | 0.1 weight part |
| Propylparaben | 0.1 weight part |
| 1,3-butylene glycol | 4 weight part |
| Methylparaben | 0.1 weight part |
| Xanthan gum | 0.1 weight part |
| Glycerin | 4 weight part |
| d-panthenol | 0.15 weight part |
| Allantoin | 0.1 weight part |
| Carbomer(2% aq. Sol) | 4 weight part |
| Triethanolamine | 0.15 weight part |
| Ethanol | 3 weight part |
| pt 41891 | 0.1 weight part |
| p-H$_2$0 | 48.3 weight part |

8-3 Preparation of Skin

| | |
|---|---|
| Compound represented by formula 1 | 0.2 weight % |
| Ethanol | 10.0 weight % |
| Polylauric acid polyoxyethylenesorbitan | 1.0 weight % |
| Methyl ρ-hydroxybenzoate | 0.2 weight % |

| | |
|---|---|
| Glycerin | 5.0 weight % |
| 1,3-butyl glycol | 6.0 weight % |
| Flavor | proper amount |
| Pigment | proper amount |
| Purified water | proper amount |
| Total | 100 |

8-4 Preparation of Nutritive Toner

| | |
|---|---|
| Compound represented by formula 1 | 0.1 weight % |
| Vaseline | 2.0 weight % |
| Sesquioleic acid sorbitan | 0.8 weight % |
| Polyoxyethyleneoleylethyl | 1.2 weight % |
| Methyl ρ-hydroxybenzoate | proper amount |
| Propylene glycol | 5.0 weight % |
| Ethanol | 3.2 weight % |
| Carboxyvinylpolymer | 18.0 weight % |
| Pigment | proper amount |
| Flavor | proper amount |
| Purified water | proper amount |
| Total | 100 |

8-5 Preparation of Essence

| | |
|---|---|
| Compound represented by formula 1 | 5.0 weight % |
| Propylene glycol | 10.0 weight % |
| Glycerin | 10.0 weight % |
| Sodium hyaluronate solution (1%) | 5.0 weight % |
| Ethanol | 3.2 weight % |
| Polyoxyethylene hydrogenated caster oil | 1.0 weight % |
| Methyl ρ-hydroxybenzoate | 0.1 weight % |
| Flavor | proper amount |
| Purified water | proper amount |
| Total | 100 |

8-6 Preparation of Pack

| | |
|---|---|
| Compound represented by formula 1 | 0.5 weight % |
| Glycerin | 5.0 weight % |
| Propylene glycol | 4.0 weight % |
| Polyvinylalcohol | 15.0 weight % |
| Ethanol | 8.0 weight % |
| Polyoxyethyleneoleylethyl | 1.0 weight % |
| Methyl ρ-hydroxybenzoate | 0.2 weight % |
| Flavor | proper amount |
| Pigment | proper amount |
| Purified water | proper amount |
| Total | 100 |

The constituents were mixed according to the preferred mixing ratio but the composition ratio can be adjusted according to regional and national preferences such as demand class, demand country and purpose of use, etc.

What is claimed is:

1. A compound represented by formula 2:

[Formula 2]

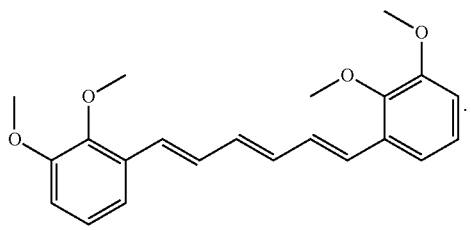

2. A composition, comprising (i) the compound of claim 1, as an active ingredient and (ii) a cosmetically acceptable carrier.

3. The composition according to claim 2, wherein the compound represented by formula 2 characteristically inhibits the expression of tyrosinase gene.

4. The composition according to claim 2, wherein the compound represented by formula 2 characteristically inhibits the expression of TRP 1 (tyrosinase-related protein 1) or TRP 2 (tyrosinase-related protein 2).

5. The composition according to claim 2, wherein the compound represented by formula 2 characteristically inhibits the expression of MITF (melanogenesis associated transcription factor) gene.

6. The composition according to claim 2, wherein the compound represented by formula 2 characteristically inhibits melanin synthesis.

7. The composition according to claim 2, wherein the compound represented by formula 2 characteristically has antioxidative effect.

8. A method for whitening skin, the method comprising: topically applying an effective amount of the composition of claim 2.

9. The method of claim 8, wherein the composition is applied as a solution, suspension, emulsion, ointment, gel, cream, spray, foam, lotion, paste, powder, oil, wax, soap, or patch.

10. The method of claim 8, wherein the effective amount is effective for exhibiting a skin whitening effect.

11. The method of claim 8, wherein the applying step is performed 1~6 times a day.

12. The composition of claim 2 further comprising one or more additional ingredient(s) selected from the group consisting of tyrosinase activity inhibitors, kojic acid, arbutin, hydroquinone, vitamin-C, and ascorbic acid.

13. The composition of claim 12, wherein the one or more additional ingredient(s) is included in the composition at the concentration of 0.0001 weight %~10 weight % of the total composition.

14. The composition of claim 2 in the form of a solution, suspension, emulsion, ointment, gel, cream, spray, foam, lotion, paste, powder, oil, wax, soap, or patch.

* * * * *

```
                        SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: synthesized nucleotide

<400> SEQUENCE: 1
actattggca acgagcggtt                                             20

<210> SEQ ID NO 2
<211> LENGTH: 20
<212> TYPE: DNA
<213> ORGANISM: Artificial Sequence
<220> FEATURE:
<223> OTHER INFORMATION: synthesized nucleotide

<400> SEQUENCE: 2
atggatgcca caggattcca                                             20

<210> SEQ ID NO 3
<211> LENGTH: 20
<212> TYPE: DNA
<213> ORGANISM: Artificial Sequence
<220> FEATURE:
<223> OTHER INFORMATION: synthesized nucleotide

<400> SEQUENCE: 3
```
cctcctggca gatcatttgt                    20

<210> SEQ ID NO 4
<211> LENGTH: 20
<212> TYPE: DNA
<213> ORGANISM: Artificial Sequence
<220> FEATURE:
<223> OTHER INFORMATION: synthesized nucleotide

<400> SEQUENCE: 4
ggcaaatcct tccagtgtgt                    20

<210> SEQ ID NO 5
<211> LENGTH: 20
<212> TYPE: DNA
<213> ORGANISM: Artificial Sequence
<220> FEATURE:
<223> OTHER INFORMATION: synthesized nucleotide

<400> SEQUENCE: 5
aggaccttga aaaccgacag                    20

<210> SEQ ID NO 6
<211> LENGTH: 20
<212> TYPE: DNA
<213> ORGANISM: Artificial Sequence
<220> FEATURE:
<223> OTHER INFORMATION: synthesized nucleotide

<400> SEQUENCE: 6
gtggatggga taagggaaag                    20

<210> SEQ ID NO 7
<211> LENGTH: 20
<212> TYPE: DNA
<213> ORGANISM: Artificial Sequence
<220> FEATURE:
<223> OTHER INFORMATION: synthesized nucleotide

<400> SEQUENCE: 7
cttggaggtc cgtgtatttg                    20

<210> SEQ ID NO 8
<211> LENGTH: 20
<212> TYPE: DNA
<213> ORGANISM: Artificial Sequence
<220> FEATURE:
<223> OTHER INFORMATION: synthesized nucleotide

<400> SEQUENCE: 8
gaccgcatca gtgaaagtgt                    20

<210> SEQ ID NO 9
<211> LENGTH: 20
<212> TYPE: DNA
<213> ORGANISM: Artificial Sequence
<220> FEATURE:
<223> OTHER INFORMATION: synthesized nucleotide

<400> SEQUENCE: 9
taccatctgt tgtggctgga                    20

<210> SEQ ID NO 10
<211> LENGTH: 20
<212> TYPE: DNA

```
<213> ORGANISM: Artificial Sequence
<220> FEATURE:
<223> OTHER INFORMATION: synthesized nucleotide

<400> SEQUENCE: 10
caagctgtcg cacacaatct                                              20
```